Jan. 14, 1958 V. A. COMPTON Plant Pat. 1,674
NECTARINE TREE
Filed Jan. 7, 1957
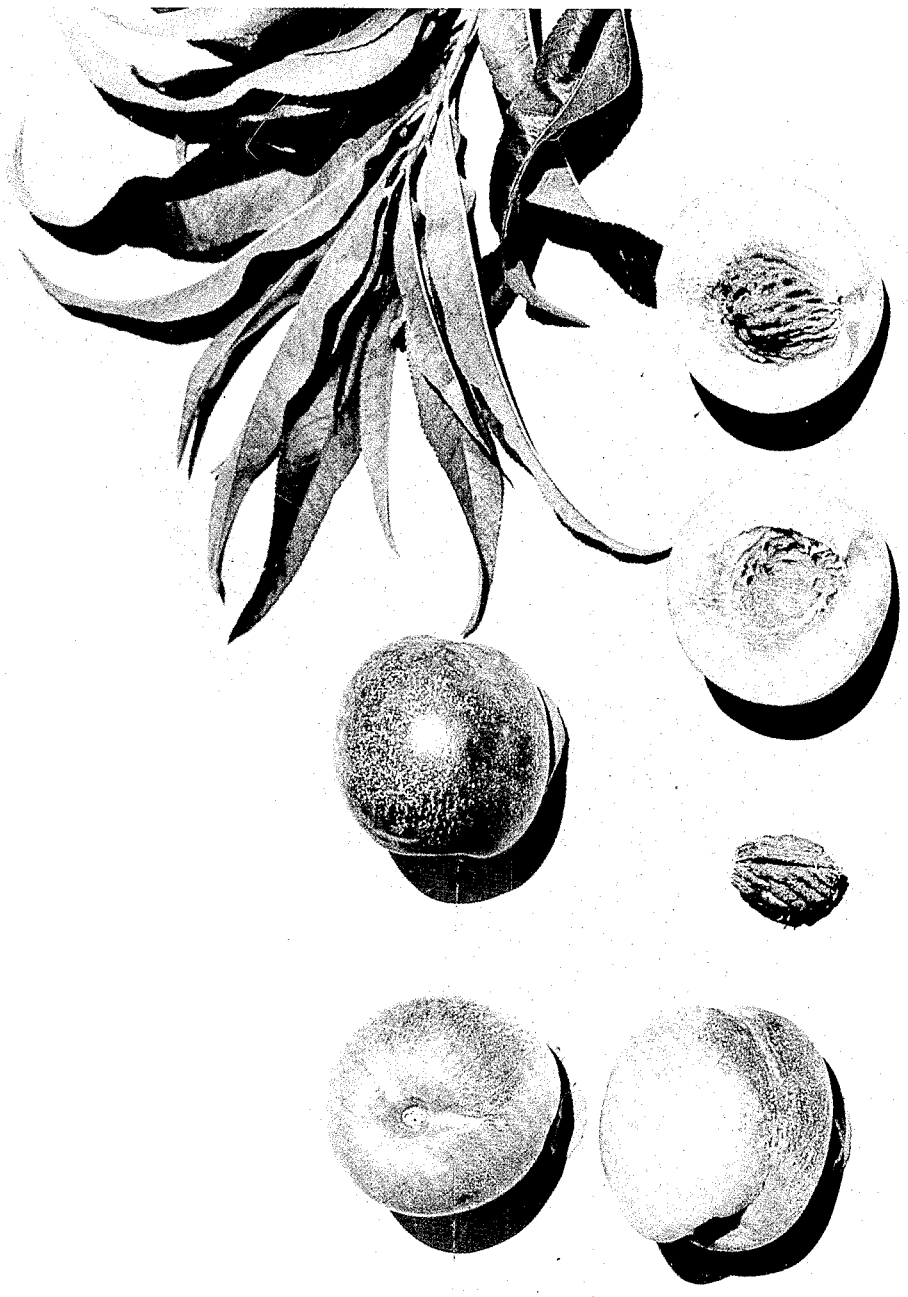
VERNA A. COMPTON
INVENTOR.
HUEBNER, BEEHLER,
WORREL & HERZIG
ATTORNEYS
BY Richard M. Worrel United States Patent Office Plant Pat. 1,674
Patented Jan. 14, 1958

1,674

NECTARINE TREE

Verna A. Compton, Ivanhoe, Calif.

Application January 7, 1957, Serial No. 632,952

1 Claim. (Cl. 47—62)

The present invention relates to a new variety of nectarine tree which is of unknown parentage.

The applicant planted seeds of unknown parentage, cared for the seedling which resulted from the planted seeds, observed the subject variety nectarine tree among the seedlings being cared for, and asexually reproduced the nectarine tree by grafting scions taken from the described seedling onto seedling peach rootings at her home at 1008 Quince Street, Ivanhoe, California. The grafts grew unusually rapidly and, as will subsequently become apparent, produced fruit which displayed certain combined characteristics of the Elberta peach and the Le Grand nectarine.

Nectarines have long been appreciated as one of the most delicious deciduous fruits when eaten freshly picked from the tree. However, they have been recognized as difficult to pick, pack and ship to market without extensive deterioration. Further, the canning of nectarines has been entirely unsatisfactory because the flesh thereof is reduced to a formless mass when cooked. In contrast with peaches which may be cooked and canned while preserving excellent flavor and physical condition, the slightest cooking for canning purposes has reduced nectarines to a sauce-like condition which is unattractive and possesses little customer appeal. Thus, it has long been an object of nurserymen and pomologists to develop a nectarine which would retain the desirable appearance and flavor of nectarines while acquiring the desirable shipping and canning characteristics of peaches.

The nectarine tree, illustrated in the accompanying drawing, which consists of a dye transfer print of a colored photograph showing characteristic fruit and foliage of the tree, possesses many advantages but the most outstanding characteristic is believed to be the ability of its fruit to retain the visual and taste appeal of the La Grand nectarine while acquiring the cooking, canning, picking, packing, storage and shipping advantages of the Elberta peach.

The following detailed description generally follows the outline suggested by U. P. Hedrick in his book entitled Systematic Pomology published in 1925 and the color terminology as employed is in accordance with the "Dictionary of Color" by Maerz and Paul, second edition.

Tree:
- *Size.*—Controlled by pruning but tending to medium.
- *Vigor.*—Initial graft and bud growth vigorous; thereafter medium vigorous.
- *Growth.*—Somewhat spreading.
- *Shape.*—Controlled by pruning but tends to spread.
- *Production.*—Heavy. Thinning required.
- *Bearing.*—Regular.

Trunk:
- *Size.*—Medium. Similar to Elberta peach tree.
- *Surface.*—Generally smooth.

Branches:
- *Size.*—Medium to stocky.
- *Surface.*—Smooth.
- *Color.*—Small branches green, plate 17, K–6 to roan, plate 7, J–7.
- *Lenticels.*—Medium.

Leaves:
- *Size.*—Medium.
- *Average length.*—Approximately six inches.
- *Width.*—Approximately one and seven-sixteenths inches.
- *Shape.*—Lanceolate, ovate base, tip acuminate.
- *Surface.*—Smooth except along midrib which is slightly rugose.
- *Marginal form.*—Minutely serrated.
- *Petiole.*—Medium thickness and average, approximately one-half inch.
- *Color.*—Light yellow green, plate 19, D–1 to green, G–3.

Glandular chararacteristics: Small singles and doubles.
- *Stem glands.*—Small singles and doubles near leaf, globose and reniform.

Flower buds:
- *Size.*—Small to medium.
- *Development.*—Early.
- *Form.*—Typically nectarine.
- *Occurrence.*—Frequently twins and triplets.

Blossoms:
- *Blooming period.*—Unusually early. Prior to Elberta peach blossoms, buds swelling as early as last week in February and blooms fully opening as early as the second week in March in the San Joaquin Valley of California.
- *Size.*—Small to medium.
- *Color.*—Springtime red, plate 2, J–9.

Fruit:
- *General exterior appearance.*—Similar to Le Grand nectarine.
- *Maturity.*—Firm to eating ripe August 10 to August 20 in San Joaquin Valley of California.
- *Size.*—Uniform. Large. Average axial diameter, two and one-half inches. Average diameter transversely in suture plane, two and one-half inches. Average transversely at right angles to suture plane two and one-fourth inches.
- *Form.*—Globose and substantially symmetrical. Somewhat truncated at stem end and minutely apiculate.
- *Suture.*—Deep and pronounced at stem end for short distance and gradually disappearing to blossom end and sometimes 20° to 30° beyond.
- *Ventral surface.*—Rounded, slightly lipped.
- *Stem cavity.*—Pronounced and substantially conically symmetrical.
- *Base.*—Truncate.
- *Apex.*—Rounded.
- *Pistil point.*—Minute.
- *Stem.*—Very short but stocky.

Skin:
- *Texture.*—Smooth.
- *Thickness.*—Medium for nectarines, tenacious to flesh, and medium tough.
- *Tendency to crack.*—Noticeable on suture near stem.
- *Color.*—Varying from clove pink, plate 6, K–5 to sunflower yellow, plate 9, L–4.
- *Pubescence.*—Lacking.

Flesh:

*General appearance.*—Quite similar to Elberta peach in texture and color.

*Flesh color.*—Deep chrome, plate 9, L–7.

*Color of surface of pit cavity.*—Pink, plate 2, K–1.

*Color of pit well.*—Gladiolus red, plate 2, K–5.

*Amygdalin.*—None.

*Juice.*—Moderate to slight as compared with other nectarines.

*Texture.*—Firm and meaty.

*Ripening.*—Relatively evenly.

*Flavor.*—Mildly acid. Somewhat similar to Elberta peach, but with noticeable characteristically nectarine flavor.

*Aroma.*—Characteristically nectarine.

*Eating quality.*—Excellent.

*Cooking quality.*—Excellent. Believed to be first nectarine capable of canning without mushing. Equivalent to Elberta peach.

*Shipping characteristics.*—Good.

Stone:

*Type.*—Free at fully ripened condition. Semi-cling at early stages and even into early picking.

*Adherence to flesh.*—Slight at maturity.

*Fibres.*—Short.

*Size.*—Large. Average length, one and five-eighth inches. Average width, approximately one and one-eighth inches. Average thickness, approximately three-fourths inch.

*Form.*—Obovate with rounded tip.

*Base.*—Truncate.

*Hilum.*—Oval.

*Apex.*—Rounded.

*Sides.*—Unequal.

*Surface.*—Medium furrowed.

*Tendency to split.*—None or slight.

*Color.*—Athenia faded rose, plate 5, I–9 to gladious red, plate 2, K–5.

Use: Canning, freezing, shipping, and local market.

Keeping quality: Good.

The tree and its fruit herein described may vary somewhat in characteristics due to climatic and soil conditions under which the variety is grown and the method of growing, including the extent of pruning and thinning. The description is that of the variety produced under ecological conditions prevailing in Tulare County of the San Joaquin Valley of the State of California.

Having thus described my new nectarine tree, I claim:

A new and distinct variety of nectarine tree, substantially as shown and described, characterized by marked similarity in the external appearance of its fruit to that of the Le Grand nectarine of Plant Patent No. 549, from which it is distinguished by firmer flesh, excellent cooking qualities, and being freestone when fully ripe; and further being characterized by the similarity in color of its flesh to that of the Elberta peach, from which is is distinguished by is glabrate, brilliantly colored skin.

No references cited.